United States Patent
Cho

(10) Patent No.: US 8,795,185 B2
(45) Date of Patent: Aug. 5, 2014

(54) PORTABLE DEVICE FOR MEASURING BLOOD PRESSURE AND METHOD THEREFOR

(75) Inventor: Jae-Geol Cho, Yongin-si (KR)

(73) Assignee: Samsung Electronics Co., Ltd (KR)

( * ) Notice: Subject to any disclaimer, the term of this patent is extended or adjusted under 35 U.S.C. 154(b) by 934 days.

(21) Appl. No.: 12/570,873

(22) Filed: Sep. 30, 2009

(65) Prior Publication Data

US 2010/0130876 A1 May 27, 2010

(30) Foreign Application Priority Data

Nov. 27, 2008 (KR) .................. 10-2008-0118604

(51) Int. Cl.
*A61B 5/02* (2006.01)
*A61B 5/022* (2006.01)
*A61B 5/021* (2006.01)
*A61B 5/00* (2006.01)

(52) U.S. Cl.
CPC ......... *A61B 5/02241* (2013.01); *A61B 5/02125* (2013.01); *A61B 5/6826* (2013.01); *A61B 5/681* (2013.01); *A61B 5/6838* (2013.01); *A61B 5/0059* (2013.01)
USPC ........... 600/483; 600/480; 600/481; 600/485; 600/500

(58) Field of Classification Search
USPC ......... 600/485, 490, 491, 492, 495, 496, 500, 600/501, 502, 503, 481, 480
See application file for complete search history.

(56) References Cited

U.S. PATENT DOCUMENTS

| 6,647,287 | B1* | 11/2003 | Peel et al. ...................... 600/513 |
| 2004/0077955 | A1 | 4/2004 | Kawanishi et al. |
| 2004/0077959 | A1 | 4/2004 | Narimatsu |
| 2005/0251059 | A1 | 11/2005 | Kim |
| 2007/0021672 | A1* | 1/2007 | Lee et al. ...................... 600/499 |
| 2007/0100247 | A1* | 5/2007 | Platt et al. ..................... 600/513 |
| 2008/0214942 | A1 | 9/2008 | Oh et al. |
| 2008/0228089 | A1* | 9/2008 | Cho et al. ...................... 600/485 |
| 2009/0018453 | A1* | 1/2009 | Banet et al. ................... 600/493 |

FOREIGN PATENT DOCUMENTS

| EP | 0 377 554 | 7/1990 |
| EP | 0 852 126 | 7/1998 |
| EP | 1967133 | 10/2008 |
| KR | 2004-64820 | 7/2004 |

* cited by examiner

*Primary Examiner* — Michael Kahelin
*Assistant Examiner* — Tho Tran
(74) *Attorney, Agent, or Firm* — The Farrell Law Firm, P.C.

(57) ABSTRACT

A portable blood pressure measuring apparatus and a method therefor are provided. In the portable blood pressure measuring apparatus, a blood pressure measurer measures a wrist or finger blood pressure being an arterial pressure at a wrist or a finger, a Pulse Wave Velocity (PWV) measurer measures a PWV, a controller controls compensation of the wrist or finger blood pressure using the PWV so that the wrist or finger blood pressure corresponds to a brachial blood pressure, and a display displays the compensated wrist or finger blood pressure.

7 Claims, 10 Drawing Sheets

PORTABLE DEVICE FOR MEASURING BLOOD PRESSURE AND METHOD THEREFOR

PRIORITY

This application claims priority under 35 U.S.C. §119(a) to a Korean Patent Application filed in the Korean Intellectual Property Office on Nov. 27, 2008 and assigned Serial No. 2008-118604, the entire disclosure of which is incorporated herein by reference.

BACKGROUND OF THE INVENTION

1. Field of the Invention

The present invention relates generally to a portable device for measuring blood pressure and a method therefor. More particularly, the present invention relates to a portable device for measuring wrist or finger arterial pressure corresponding to brachial arterial pressure and a method therefor.

2. Description of the Related Art

Blood pressure is one of the most useful vital signs for human health care. Clinically, blood pressure provides an index by which abnormalities of the circulatory system, including the heart and blood vessels, can be diagnosed. Blood pressure outside a normal range requires consistent care. Arterial pressure changes with cardiac pulsation. The peak pressure the arteries feel when the ventricles are contracting and pushing the blood out into the arteries is called systolic pressure. Even when the ventricles are relaxing and filling back up with blood, the elasticity of the walls of the arteries maintains some blood pressure, and thus the blood pressure does not drop to zero. This lower level of blood pressure is called diastolic pressure.

Nervousness often results in a high blood pressure measurement when a person visits a clinic. Since blood pressure varies with a variety of factors, it is difficult to get an accurate blood pressure measurement at one time. Hence, a home-use electronic blood pressure monitor is necessary to enable users to constantly measure their blood pressures at their homes. The most widely used automatic electronic blood pressure monitor operates by volume oscillometry. The volume oscillometry scheme measures blood pressure based on oscillations that are generated by raising or dropping pressure to the arteries with use of a cuff. In this measuring method, the cuff pressure at which the pulse arising from cardiac pulsation has a maximum amplitude that is estimated to be a mean blood pressure. Herein, the systolic and diastolic pressures are estimated to be cuff pressures having 45 to 57% and 74 to 82% of the maximum amplitude, respectively.

FIG. 1 is a graph illustrating blood pressure measurements based on oscillation pressures of a cuff. Referring to FIG. 1, the ratio of a systolic amplitude to a maximum amplitude and the ratio of a diastolic amplitude to the maximum amplitude are called characteristic ratios, which vary with individuals. It is known that the characteristic ratios are greatly affected by cuff characteristics, the characteristics of artery vessels, the shape and amplitude of arterial pressure waves, etc.

At present, most blood pressure monitors measure blood pressure in an upper arm at heart level. For measurement convenience, products for measuring blood pressure in a wrist or a finger using a cuff have been developed and commercialized.

Such a wrist- or finger-type blood pressure monitor is smaller than the upper arm-type monitor. Due to the small size, the wrist- or finger-type blood pressure monitor is portable and obviates the need to take off a portion of a patient's clothing for pressure measuring, thus allowing blood pressure measuring at any time. However, because a wrist or finger arterial signal is weaker than a brachial arterial signal, it basically has a low Signal-to-Noise Ratio (SNR). Therefore, the wrist- or finger-type blood pressure monitor is less accurate than the upper arm-type one.

Blood pressure may differ at different artery positions due to a plurality of factors. Hence, the wrist- or finger-type blood pressure monitor may give a different blood pressure measurement from that of the upper arm-type one. As a consequence, blood pressure measurements of the wrist- or finger-type blood pressure monitor may be less reliable to users.

A conventional wrist- or finger-type blood pressure monitor measures an arterial pressure by oscillometry, like the upper arm-type blood pressure monitor. If the blood pressure monitor is precise and the brachial arterial pressure is equal to the wrist- or finger arterial pressure, a pressure at the upper arm should be equal to a pressure at the wrist or finger which is leveled at the heart height.

However, the brachial arterial pressure is different from the wrist or finger arterial pressure due to the characteristics of blood, flow, and the differences between individuals.

That is, a measured wrist or finger arterial pressure of a user may be higher or lower than a measured brachial arterial pressure for the same individual.

FIG. 2 illustrates characteristics of blood pressure and waveform changes with respect to the positions of arteries. In FIG. 2, pulse pressure changes with respect to the distances of the arteries to an aorta are shown, as well as pulse pressure changes that vary with age. That is, the difference between systolic and diastolic pressures increases at an artery more remote from an aorta at younger ages due to the overlap of reflective waves. At older ages, the difference is zero or may increase. Even individuals of the same age may differ in the systolic-diastolic difference. Therefore, when a user familiar with the upper arm-type blood pressure monitor popular in clinics uses the wrist- or finger-type blood pressure monitor, for use convenience or portability, he may be confused with blood pressure measurements.

SUMMARY OF THE INVENTION

The present invention has been made to address at least the above problems and/or disadvantages, and to provide at least the advantages described below.

An aspect of an embodiment of the present invention provides a portable blood pressure measuring apparatus for giving a user a wrist or finger arterial pressure compensated to correspond to a brachial arterial pressure that differs in individuals, and a method therefor.

In accordance with an aspect of an embodiment of the present invention, there is provided a portable blood pressure measuring apparatus in which a blood pressure measurer measures a blood pressure being an arterial pressure at a wrist or a finger, a Pulse Wave Velocity (PWV) measurer measures a PWV, a controller controls compensation of the blood pressure using the PWV so that the blood pressure being an arterial pressure at a wrist or finger corresponds to a brachial blood pressure, and a display displays the compensated blood pressure.

In accordance with another aspect of an embodiment of the present invention, there is provided a portable blood pressure measuring method in which a blood pressure being an arterial pressure at a wrist or a finger is measured in blood pressure measuring mode, a PWV is measured, the blood pressure is compensated using the PWV so that the blood pressure being an arterial pressure at a wrist or finger corresponds to a brachial blood pressure, and the compensated blood pressure is displayed.

BRIEF DESCRIPTION OF THE DRAWINGS

The above and other aspects, features and advantages of certain embodiments of the present invention will be more apparent from the following detailed description taken in conjunction with the accompanying drawings, in which.

DETAILED DESCRIPTION OF EMBODIMENTS OF THE INVENTION

Figure 1:
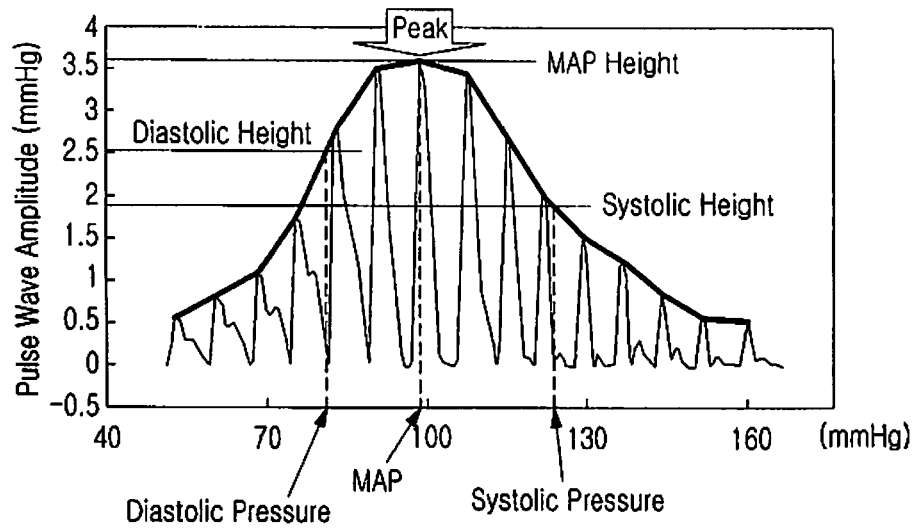
FIG. 1 is a graph illustrating blood pressure measurements based on oscillation pressures of a cuff.
Figure 2:
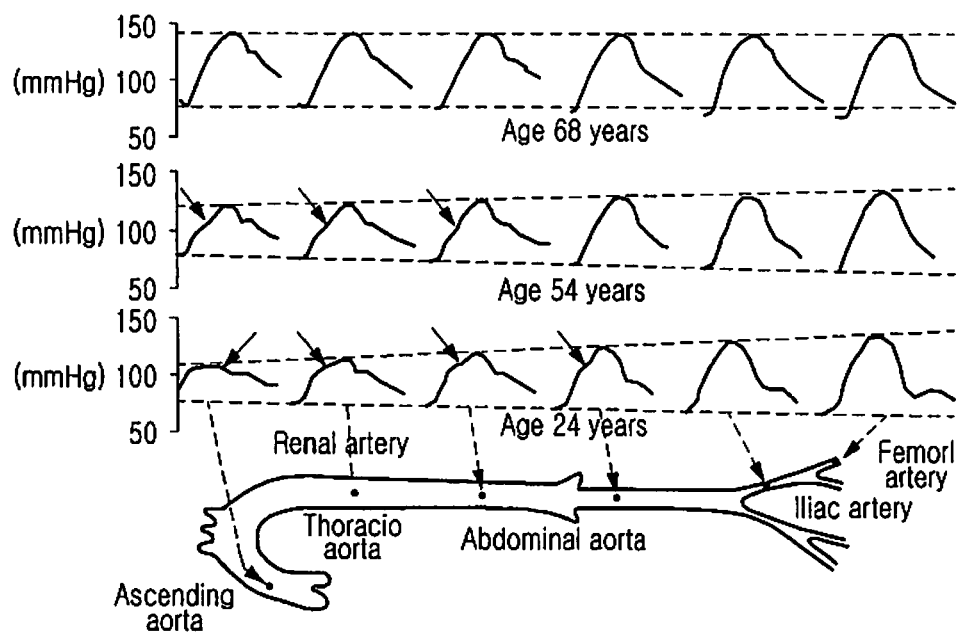
FIG. 2 illustrates characteristics of blood pressure and waveform changes with respect to the positions of arteries.

The matters defined in the description such as a detailed construction and elements are provided to assist in a comprehensive understanding of the embodiments of the invention. Accordingly, those of ordinary skill in the art will recognize that various changes and modifications of the embodiments described herein can be made without departing from the scope and spirit of the invention. Also, descriptions of well-known functions and constructions are omitted for clarity and conciseness. Throughout the drawings, the same drawing reference numerals will be understood to refer to the same elements, features and structures.

To calculate the difference between brachial blood pressure and radial blood pressure, information by which to measure or estimate an individual deviation is necessary in a conventional blood pressure measuring method. The information may be the velocity of pulse waves from which blood pressure is measured. Accordingly, Pulse Wave Velocity (PWW) is used to compensate for an individual radial-brachial pressure difference in accordance with the present invention.

Figure 3:
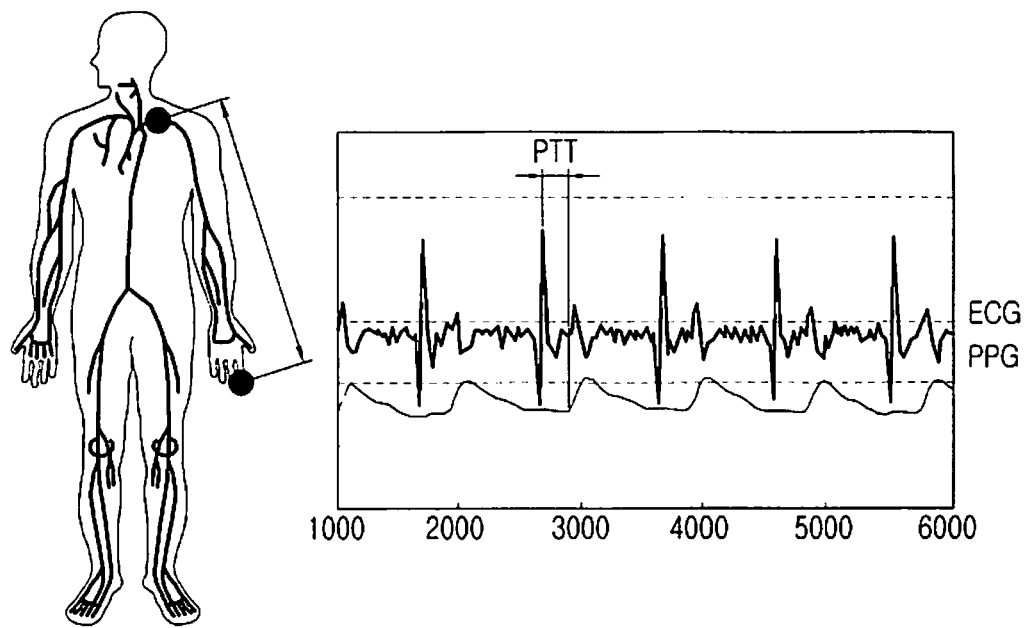
FIG. 3 illustrates measuring of a Pulse Wave Velocity (PWV) using an ElectroCardioGram (ECG) signal and a PhotoPlethysnoGraphy (PPG) signal.

FIG. 3 illustrates measuring of a PWV using an ElectroCardioGram (ECG) signal and a PhotoPlethysnoGraphy (PPG) signal. Referring to FIG. 3, the time difference between an R-peak of the ECG signal and start of a PPG signal measured by an optical sensor in a portable blood pressure measuring apparatus carried around a wrist or a finger, namely a Pulse Transit Time (PTT) is the time taken for the PPG signal to reach a measurement spot as the ventricles are contracted. A PWV is calculated by dividing the distance between the heart and the measurement spot of the PPG signal by the PTT. The PWV is widely used as an arterial stiffness index.

Figure 4A:
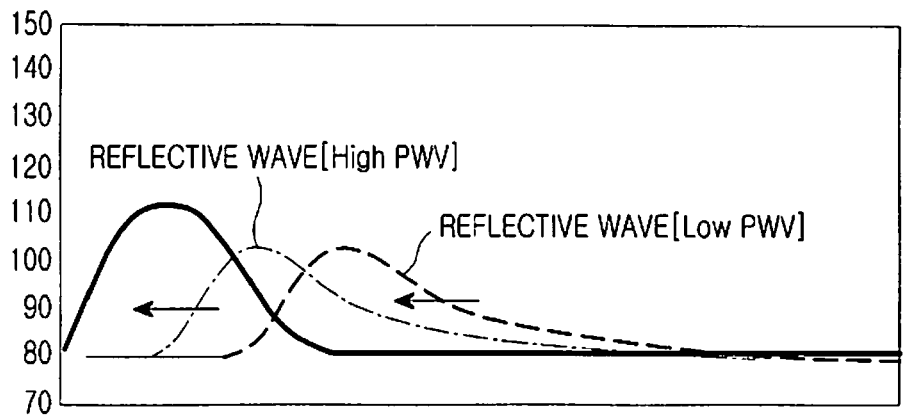
FIGS. 4A, 4B and 4C illustrate pulse wave overlap characteristics according to PWVs.
Figure 4B:
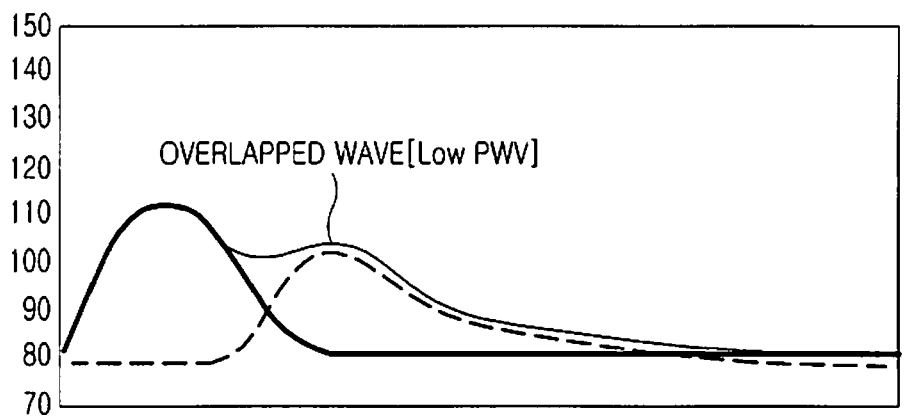
Figure 4C:
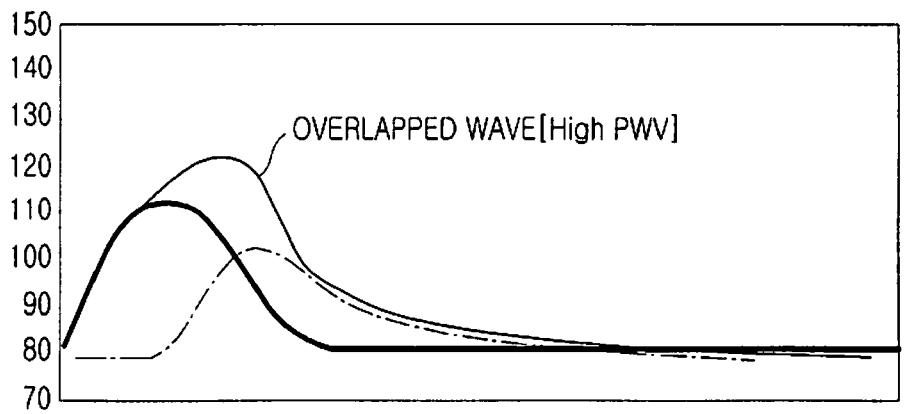

FIGS. 4A, 4B and 4C illustrate pulse wave overlap characteristics according to PWVs. A PPG signal generated from ventricular contraction causes a reflective wave at an aortic bifurcation or an aortic termination. As illustrated in FIG. 4A, the magnitude and shape of a PPG signal at a certain spot on an artery are determined by the overlap between the original PPG signal and a reflective wave.

Referring to FIG. 4B, if the PWV is low, the overlap between the reflective wave and the PPG signal does not increase the maximum pressure of the PPG signal. On the other hand, when the PWV is high, as illustrated in FIG. 4C, if the overlap between the reflective wave and the PPG signal increases the maximum pressure of the overlapped wave, that is, the systolic pressure is above the maximum pressure of the original PPG signal, the increase of the PWV also increases the systolic pressure due to the overlap.

The overlap of the PPG signal also depends on the distance from a spot where the reflective wave is generated, as well as the PWV.

If a PPG signal measured at a wrist or a finger near the aortic termination where a reflective wave is created is different from a PPG signal measured at the brachial aorta relatively far from the aortic termination, in terms of magnitude and shape, this difference is caused by a difference in overlap time, as described above.

When the PWV is low, for example, when a wave having the shape illustrated in FIG. 4C is formed at the wrist aorta and a wave having the shape illustrated in FIG. 4B is formed at the brachial aorta, the systolic pressure changes as much as the difference between the maximum pressures illustrated in FIGS. 4B and 4C.

When the PWV increases, the maximum pressure of the wrist or finger aorta increases due to wave overlap. As a consequence, the maximum pressure difference between the wrist or finger aorta and the brachial aorta increases.

If arteriosclerosis causes an extremely high PWV, the waves of the wrist or finger and brachial aortas have the shape illustrated in FIG. 4C. In this case, the maximum pressure difference between the wrist or finger aorta and the brachial aorta may drop.

In general, the difference between the radial or finger artery pressure and the brachial pressure measured at the same height (i.e. the height measured from the heart level) tends to increase as the PWV is higher.

Figure 5:
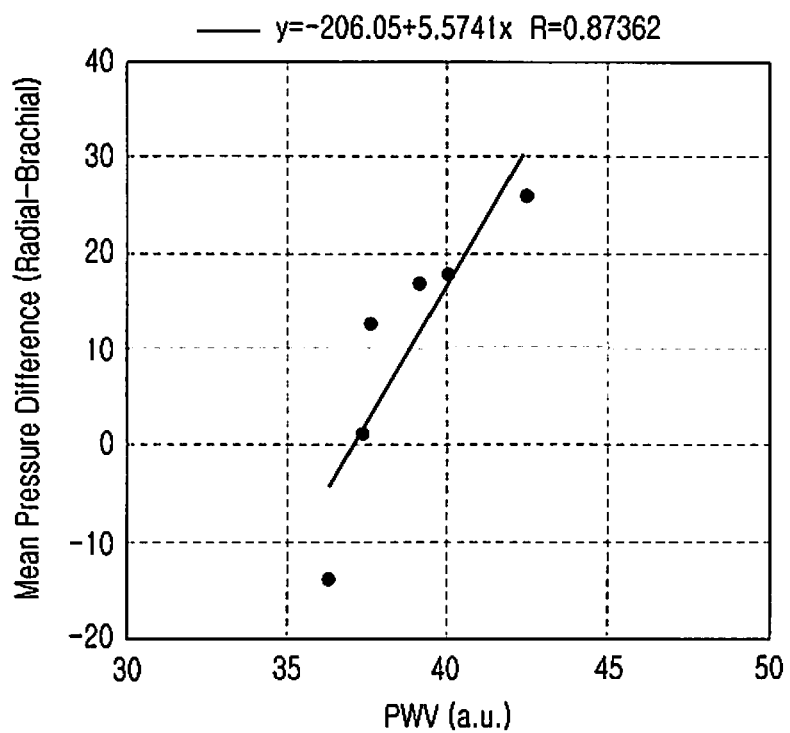
FIG. 5 is a graph illustrating a relationship between PWV and radial and brachial blood pressures.

FIG. 5 is a graph illustrating a relationship between PWVs and radial and brachial blood pressures. The graph shows results of a test that was performed to verify the trend that the difference between the radial pressure and the brachial pressure increases with the PWV.

Blood pressures of six persons were measured at heart level using a cuff-based upper arm blood pressure monitor (A&D, UA-767) and a cuff-based wrist blood pressure monitor (Citizen, CH-656C). For each person at the same position, a PWV is measured from the ECG signals of both hands and a PPG signal of a finger measured by a transmissive optical sensor. The PWV and the mean difference between the radial pressure and the brachial pressure were plotted as a graph. As expected, the graph indicates that the difference between the radial pressure and the brachial pressure increases with the PWV.

Figure 6C:
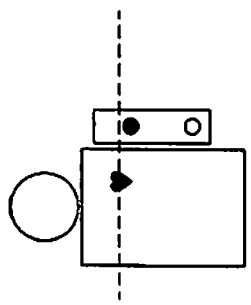
FIG. 6C illustrate when the positions of the wrists is lower than the heart level.
Figure 6D:
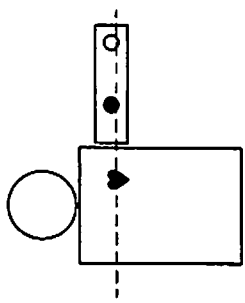
FIG. 6D illustrate when the positions of the wrists is same the heart level.
Figure 6E:
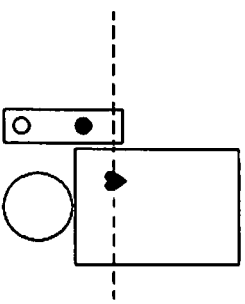
FIG. 6E illustrate when the positions of the wrists is same the heart level.
Figure 6B:
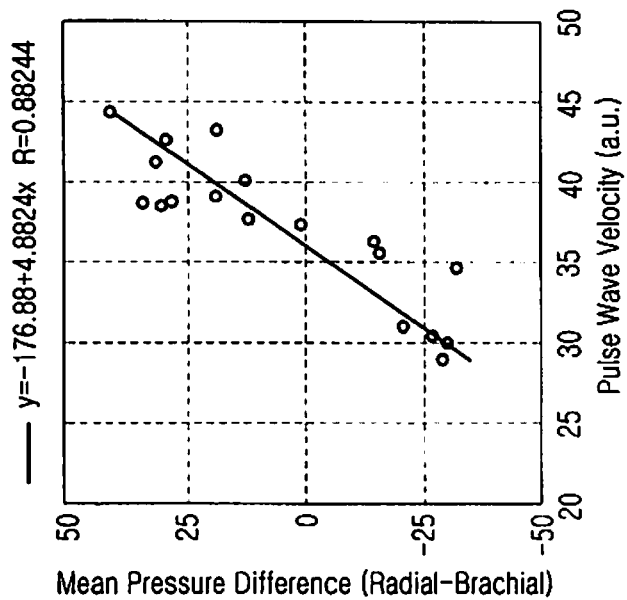
FIG. 6B is a graph illustrating a relationship between PWV and radial-brachial diastolic pressure difference.
Figure 6A:
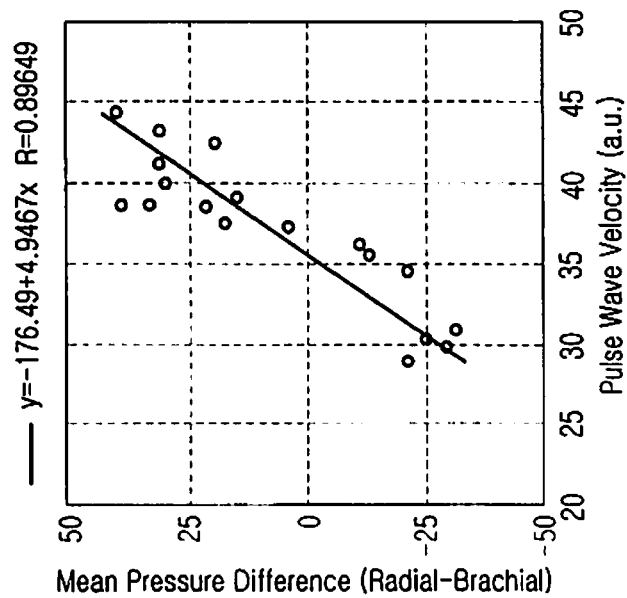
FIG. 6A is a graph illustrating a relationship between PWV and radial-brachial systolic pressure difference.

To find out whether the characteristics illustrated in FIG. 5 also apply to a wider range of PWVs and a wider range of blood pressures, as illustrated in FIGS. 6C, 6D and 6E the positions of the wrists of the six persons were changed with respect to the heart level, thereby causing an about −30 to 40 mm Hg-difference between the radial pressure and the brachial pressure. In the case illustrated in FIG. 6, it is revealed that both the systolic and diastolic pressure differences between the radial pressure and the brachial pressure have a correlation coefficient of about 0.9.

The operation of the portable blood pressure measuring apparatus based on the relationship between the PWV and the radial-brachial difference is described in detail with reference to FIGS. 7 to 10.

Figure 7:
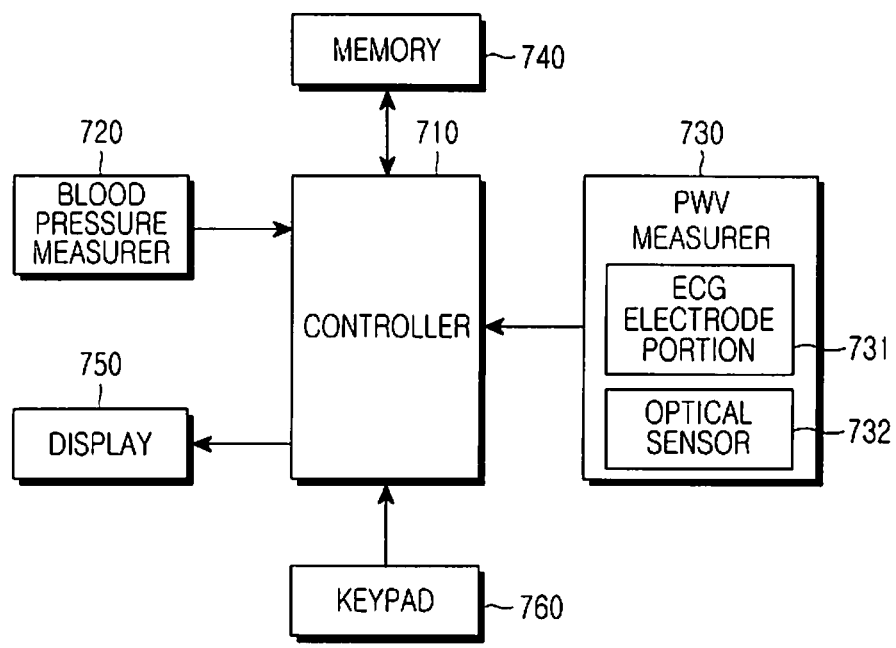
FIG. 7 is a block diagram of a portable blood pressure measuring apparatus according to an exemplary embodiment of the present invention.
Figure 8:
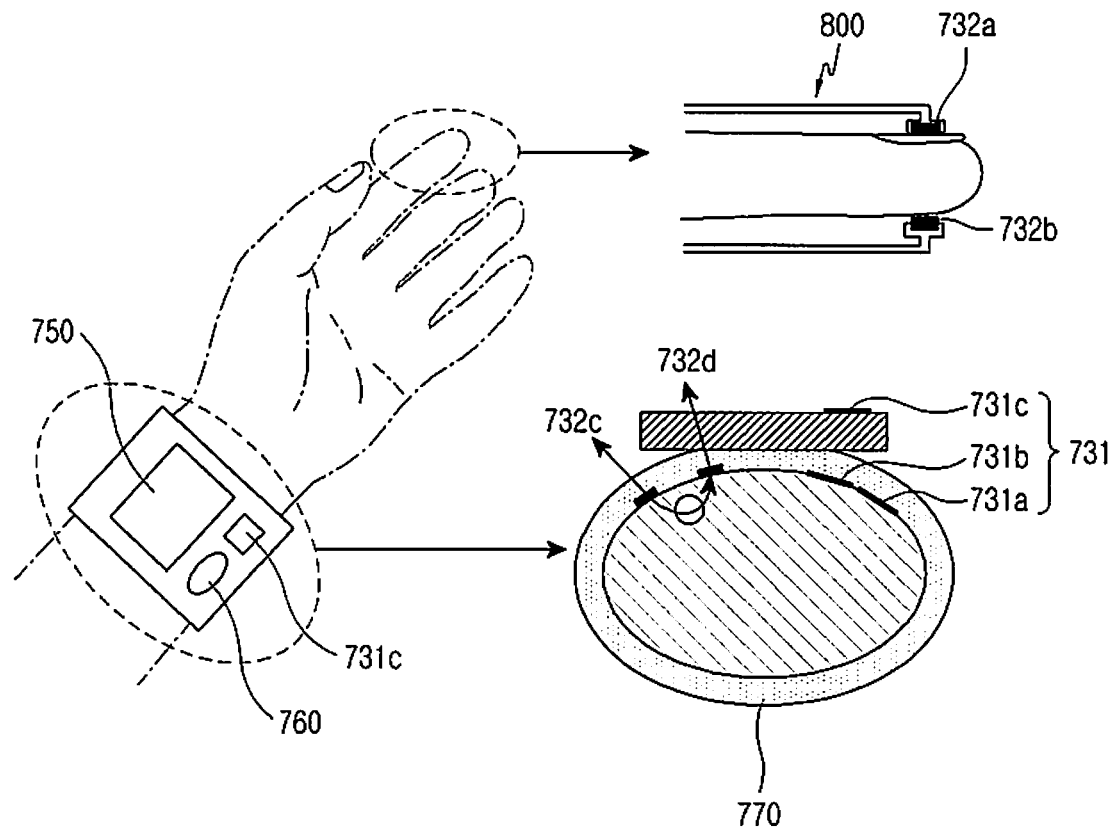
FIG. 8 illustrates a portable blood pressure measuring apparatus according to an exemplary embodiment of the present invention.
Figure 9:
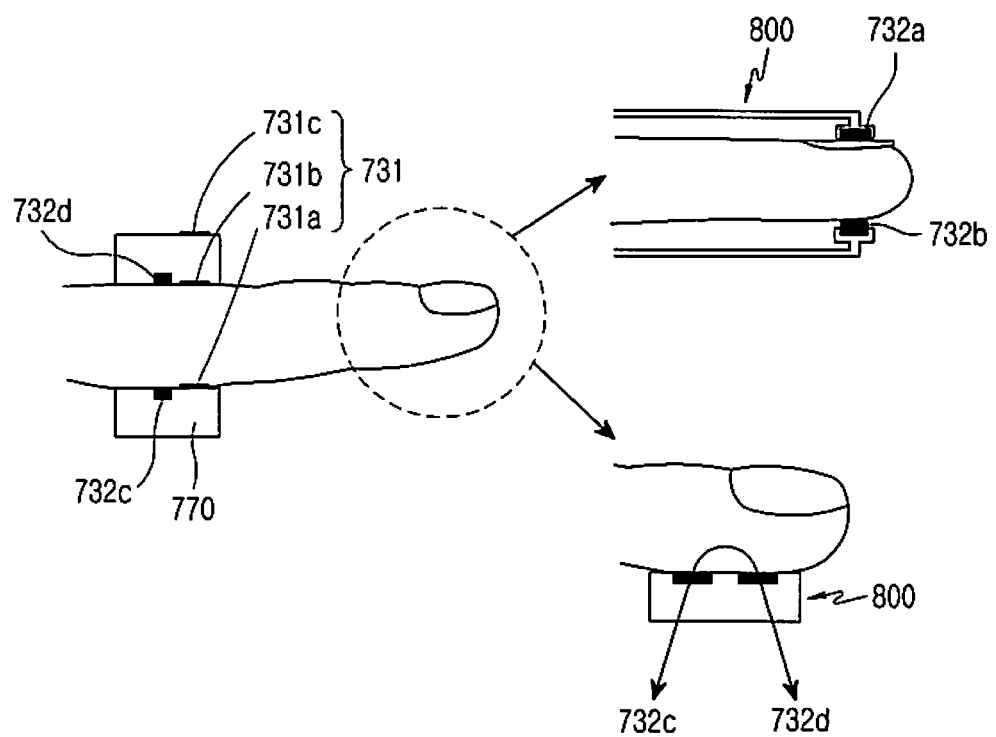
FIG. 9 illustrates a portable blood pressure measuring apparatus according to another exemplary embodiment of the present invention.
Figure 10:
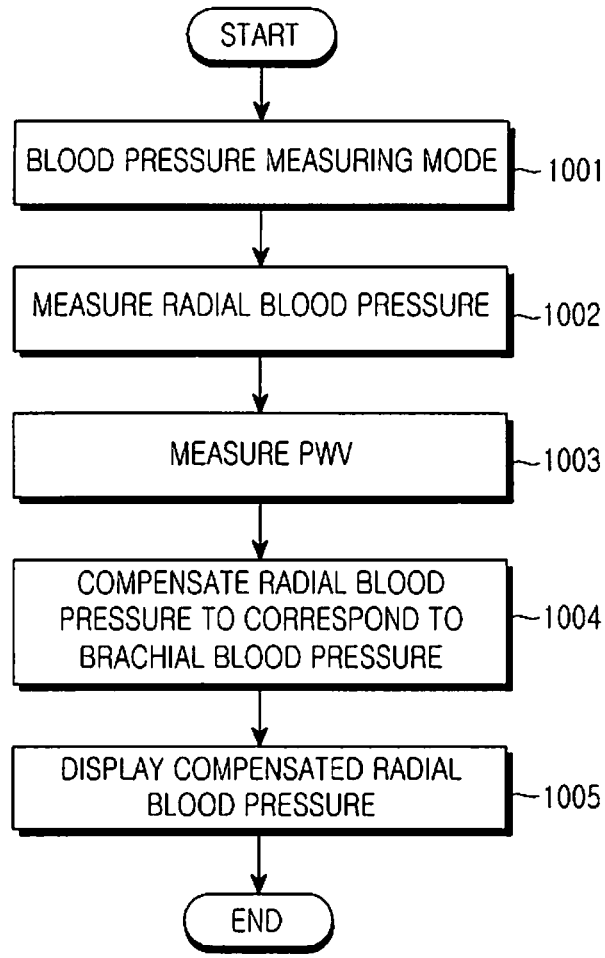
FIG. 10 is a flowchart illustrating an operation for measuring blood pressure in a portable blood pressure measuring apparatus according to an exemplary embodiment of the present invention.

FIG. 7 is a block diagram of a portable blood pressure measuring apparatus according to a preferred embodiment of the present invention, FIG. 8 illustrates a portable blood pressure measuring apparatus according to embodiment of the present invention, FIG. 9 illustrates a portable blood pressure measuring apparatus according to another preferred embodiment of the present invention, and FIG. 10 is a flowchart illustrating an operation for measuring blood pressure in a portable blood pressure measuring apparatus according to an preferred embodiment of the present invention.

Referring to FIG. 7, a pressure measurer 720 measures a wrist or finger and provides the pressure measurement to a controller 710. Also provided are display 750, memory 740 and keypad 760.

A PWV measurer 730 measures a PWV, including an ECG electrode portion 731 and an optical sensor 732.

The ECG electrode portion 731 includes at least two electrodes. It is assumed that the ECG electrode portion 731 includes three electrodes in accordance with the exemplary embodiment of the present invention. Two of the three electrodes are provided inside a cuff of the portable blood pressure measuring apparatus and the other electrode is provided outside the cuff. Alternatively, one of the three electrodes is inside the cuff, while the other two electrodes are positioned outside the cuff.

The optical sensor 732 includes a light source and a light receiving device. The optical sensor 732 may reside in the cuff or in an additional device attached to a finger.

The structure of the PWV measurer 730 will be described in detail with reference to FIGS. 8 and 9. FIG. 8 illustrates a wrist-type blood pressure measuring apparatus. Three electrodes 731a, 731b and 731c for measuring an EGC signal are added to a conventional blood pressure monitor cuff 770. An optical sensor 732 for measuring a PPG signal is provided inside a cuff 770 that contacts a wrist aorta portion or is provided in an additional device 800 that wraps around a finger.

As illustrated in FIG. 8, regarding ECG electrodes, two ECG electrodes (e.g. a (−) electrode 731a and a GND electrode 731b) are provided at a portion that contacts with an arm around which the cuff 770 is wrapped, and one ECG electrode (e.g. a positive (+) electrode 731c) is provided on a display 750 or outside the cuff 770. Alternatively, the electrode 731c may be positioned inside the cuff 770 and the two electrodes 731a and 731b may be positioned outside the cuff 770.

When blood pressure is measured, the ECG electrodes within the cuff 770 are brought into contact with the arm around which the cuff 770 is wrapped. Therefore, an ECG is measured by contacting a finger from the hand of the arm without the cuff 770.

As illustrated in FIG. 8, pulse waves by which to measure the PWV may be measured by adding a transmissive optical sensor 732a and 732b to the additional device 800 installed to the finger or a reflective optical sensor (a light source 732c and a light receiving device 732d) inside the cuff 770. Especially when a PPG signal is measured at the wrist aorta, it is preferable to dispose the light source 732c and the light receiving device 732d such that the aorta is positioned between the light source 732c and the light receiving devices 732d.

FIG. 9 illustrates a finger-type blood pressure measuring apparatus. Like the writs-type blood pressure measuring apparatus, the finger-type blood pressure measuring apparatus preferably additionally has ECG electrodes 730 inside and outside the cuff 770 in order to measure the PWV. Since the finger aorta is small, oscillation may be measured by use of optical sensors 732a and 732b instead of pressure oscillation of the cuff 770. In this case, the optical sensors 732a and 732b are added inside the cuff 770 to apply the oscillometry method, compared to the wrist-type blood pressure measuring apparatus. The PWV may be measured using the optical sensors 732a and 732b.

However, since the PWV changes when pressure is applied to arterial vessels by pressing the cuff 770, it is preferred that a transmissive or reflective optical sensor is additionally provided in an additional device 800 attached to the tip of the finger, besides the optical sensor within the cuff.

The controller 710 providers overall control to the portable blood pressure measuring apparatus. Upon receipt of a wrist or finger pressure value measured by the pressure measurer 720, the controller 710 controls compensation of the received wrist or finger pressure value using the PWV received from the PWV measurer 730 by an equation for compensating the wrist or finger pressure to correspond to a brachial pressure.

The controller 720 controls the compensated wrist or finger pressure to be displayed on the display 750.

The memory 740 stores the compensation equation which has been selected from among the following compensation equations:

$$P_{brachial} = a + b \times P_{wrist\ or\ finger} + c \times PWV \tag{1}$$

$$P_{brachial} = a + b \times P_{wrist\ or\ finger} + c \times PWV + d \times PWV^2 \tag{2}$$

$$P_{brachial} = a + b \times P_{wrist\ or\ finger} + c \times PWV + d \times PWV^2 e \times PWV^3 \tag{3},$$

where $P_{brachial}$ is a brachial blood pressure $P_{wrist\ or\ finger}$ is a blood pressure measured at the wrist or finger, PWV is a PWV, and a, b, c, d and e are empirical constants for compensating the wrist or finger pressure value.

The compensation equation can also be empirically selected by a developer of the portable blood pressure measuring apparatus. The developer determines the correlation coefficients between wrist or finger and brachial pressure difference and the PWV for both systolic and diastolic pressures, selects an equation that approximates the wrist or finger pressure to the brachial pressure from among the equations as described above, and stores the equation in the memory 740. Alternatively, the developer derives more than the above compensation equations by performing testing based on an equation $P_{brachial}=f(P_{wrist\ or\ finger}, PWV)$, pursuant to the relationship between PWV and wrist or finger-brachial pressure difference illustrated in FIG. 6.

In accordance with an embodiment of the present invention, the memory 740 stores all of equations 1 through 3 so that only a user-selected equation is used in pressure measuring mode, and the memory 740 preferably also stores the compensated radial pressure.

The display 750 displays the wrist or finger pressure compensated to correspond to the brachial pressure in the pressure measuring mode. The keypad 760 includes function keys by which functions of the portable blood pressure measuring apparatus are set.

A blood pressure measuring operation of the portable blood pressure measuring apparatus illustrated in FIGS. 7, 8 and 9 is described in detail with reference to FIG. 10.

FIG. 10 is a flowchart illustrating an operation for measuring blood pressure in a portable blood pressure measuring apparatus according to a preferred embodiment of the present invention.

Referring to FIG. 10, upon selection of pressure measuring mode by key input of the keypad 760, the controller 740 senses the pressure measuring mode and transitions the portable blood pressure measuring apparatus to a pressure measuring mode in step 1001.

The pressure measurer 720 measures a wrist or finger pressure by the oscillation of the cuff and transmits the wrist or finger pressure to the controller 740 in the pressure measuring mode in step 1002.

In step 1003, the PWV measurer 730 measures a PWV through the ECG electrode portion 731 and the optical sensor 732 and provides the PWV to the controller 740.

Upon receipt of the wrist or finger pressure and the PWV, the controller 740 compensates the wrist or finger pressure to correspond to a brachial pressure utilizing the compensation equation stored in the memory 740, in step 1004.

In step 1005, the controller 740 displays the compensated wrist or finger pressure on the display 750.

Figure 11A:
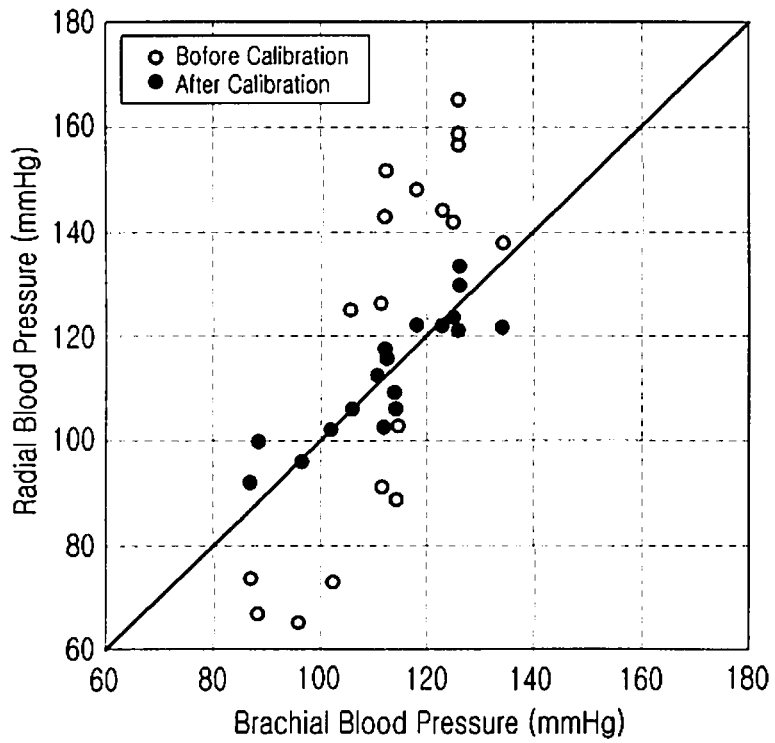
FIGS. 11A and 11B are graphs illustrating blood pressures measured by a portable blood pressure measuring apparatus according to an exemplary embodiment of the present invention.
Figure 11B:
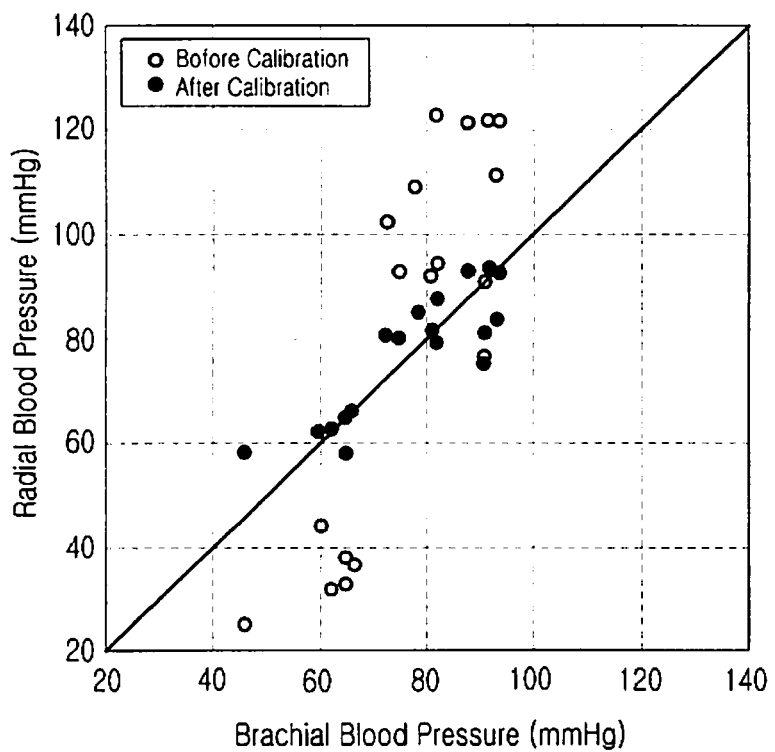

FIGS. 11A and 11B are graphs illustrating blood pressures measured by a portable blood pressure measuring apparatus according to a preferred embodiment of the present invention. In FIG. 11, in the case of an about −30 to 40 mm Hg difference between the radial pressure and the brachial pressure as illustrated in FIG. 6, the pressure difference is decreased by the procedure of FIG. 10. The compensation equation used herein is equation 1.

As is apparent from the above description, the portable blood pressure measuring apparatus and method of the present invention effectively eliminate the difference between a radial pressure and a brachial pressure for individuals using a PWV. Therefore, the radial pressure is compensated to correspond to the brachial pressure, for the user. Since consistency is secured between an upper arm blood pressure monitor used in a clinic and a wrist-type or finger-type blood pressure monitor, instant blood pressure measurement and management is obtained.

Embodiments of the present invention can also be embodied as computer-readable codes on a computer-readable recording medium. The computer-readable recording medium includes data storage devices that store data for subsequent use by a computer system. Examples of the computer-readable recording medium include, but are not limited to, Read-Only Memory (ROM), Random-Access Memory (RAM), CD-ROMs, magnetic tapes, floppy disks, optical data storage devices, and carrier waves (such as data transmission through the Internet via wired or wireless transmission paths). The computer-readable recording medium can also be distributed over network-coupled computer systems so that the computer-readable code is stored and executed in a distributed fashion. Also, function programs, codes, and code segments for accomplishing the present invention can be easily construed as within the scope of the invention by programmers skilled in the art to which the present invention pertains.

While the invention has been shown and described with reference to certain embodiments of the present invention thereof, it will be understood by those skilled in the art that various changes in form and details may be made therein without departing from the spirit and scope of the present invention as defined by the appended claims and their equivalents.

What is claimed is:

1. A portable blood pressure measuring apparatus comprising:
a blood pressure measurer for measuring a wrist or finger blood pressure, wherein the wrist or finger blood pressure is an arterial pressure measured at a wrist or a finger;
a Pulse Wave Velocity (PWV) measurer for measuring a PWV;
a controller for controlling compensation of the wrist or finger blood pressure using the measured PWV so that the wrist or finger blood pressure corresponds to a brachial blood pressure; and
a display for displaying the compensated wrist or finger blood pressure,
wherein the controller controls the compensation of the wrist or finger blood pressure using one of the following equations:

$$P_{brachial}=a+b\times P_{wrist\ or\ finger}+c\times PWV$$

$$P_{brachial}=a+b\times P_{wrist\ or\ finger}+c\times PWV+d\times PWV^2$$

$$P_{brachial}=a+b\times P_{wrist\ or\ finger}+c\times PWV+d\times PWV^2+e\times PWV^3$$

where $P_{brachial}$ is a brachial blood pressure $P_{wrist\ or\ finger}$ is a blood pressure measured at the wrist or finger, PWV is a PWV, and a, b, c, d and e are empirical constants for compensating the wrist or finger blood pressure value.

2. The portable blood pressure measuring apparatus of claim 1, wherein the PWV measurer includes an ElectroCardioGram (ECG) electrode portion for measuring an ECG signal.

3. The portable blood pressure measuring apparatus of claim 2, wherein the ECG electrode portion includes a first electrode positioned inside a cuff of the portable blood pressure measuring apparatus and a second electrode positioned outside the cuff.

4. The portable blood pressure measuring apparatus of claim 1, further comprising a memory for pre-storing the equation used by the controller to control the compensation of the wrist or finger blood pressure.

5. The portable blood pressure measuring apparatus of claim 1, wherein the PWV measurer includes an optical sensor for measuring a PhotoPlethysnoGraphy signal.

6. The portable blood pressure measuring apparatus of claim 5, wherein the optical sensor includes a light source and a light receiving device, and the optical sensor is positioned inside a cuff of the portable blood pressure measuring apparatus.

7. The portable blood pressure measuring apparatus of claim 5, wherein the optical sensor includes a light source and a light receiving device provided at an additional device configured to attach to the finger.

* * * * *